United States Patent [19]

McDonald et al.

[11] 4,188,120
[45] Feb. 12, 1980

[54] RADIOIODINE DETECTOR BASED ON LASER INDUCED FLUORESCENCE

[75] Inventors: Jimmie R. McDonald, Upper Marlboro, Md.; Andrew P. Baronavski, Alexandria, Va.

[73] Assignee: The United States of America as represented by the Secretary of the Navy, Washington, D.C.

[21] Appl. No.: 867,412

[22] Filed: Jan. 6, 1978

[51] Int. Cl.² .............................................. G01J 3/30
[52] U.S. Cl. .................................. 356/318; 250/458; 250/459; 331/94.5 G
[58] Field of Search .................. 356/85, 318; 250/364, 250/458, 459, 461 R

[56] References Cited

U.S. PATENT DOCUMENTS

| | | | |
|---|---|---|---|
| 3,826,920 | 7/1974 | Woodroffe et al. | 250/461 R |
| 3,829,696 | 8/1974 | Birnbaum | 250/461 R |
| 3,967,120 | 6/1976 | Ashe et al. | 250/328 |
| 3,982,129 | 9/1976 | Lattin et al. | 250/364 |

OTHER PUBLICATIONS

"Laser-Induced Fluorescence in a Molecular Beam of Iodine" Ezekiel et al; Physical Review Letters; vol. 20, #3; Jan. 15, 1968; pp. 91 & 92.

Primary Examiner—Vincent P. McGraw
Attorney, Agent, or Firm—R. S. Sciascia; Philip Schneider; David G. Rasmussen

[57] ABSTRACT

The invention involves the measurement of the concentration of the radioisotope $^{129}I_2$ in the presence of a gas. The invention uses a laser to excite a sample of the $^{129}I_2$ in a sample gas chamber and a reference sample of a known concentration of $^{129}I_2$ in a reference gas chamber. The $^{129}I_2$ in the sample and reference gas chamber each gives off fluorescence emissions which are received by photomultipliers which provide signals to a detector. The detector uses a ratioing technique to determine the concentration of $^{129}I_2$ in the sample gas chamber.

9 Claims, 4 Drawing Figures

RADIOIODINE DETECTOR BASED ON LASER INDUCED FLUORESCENCE

BACKGROUND OF THE INVENTION

1. Field of the Invention

The invention relates to a method and apparatus for measuring the concentration of the $^{129}I_2$ isotope in a gas. More specifically the invention relates to the use of a laser to cause the $^{129}I_2$ isotope to produce fluorescence emission from which the concentration of the isotope may be measured while not exciting other iodine istope atoms, such as $^{127}I$ and $^{131}I$.

DESCRIPTION OF THE PRIOR ART

Of the six major iodine isotopes produced in nuclear reactors, $^{129}I_2$ (hereinafter I-129) represents only about 1% of the main iodine fission product yield. Although this isotope has the lowest specific activity and the lowest energy decay products, after a few days of cooling outside the reactor the major iodine isotope present is I-129, because the next longest-lived isotope $^{131}I$ has a decay half-life of 8.0 days. In view of the very long I-129 half-life of about 17 million years attention has been directed to its cumulative effects. In spent fuel processing, I-129 will have to be recovered and stored indefinitely because of its longevity.

One means of recovering and storing I-129 is with charcoal filters. A problem that occurs is that a charcoal filter may allow small amounts of iodine including I-129 through the filter (called critical filter breakthrough). An iodine monitor is needed to detect such iodine leakage.

Prior-art iodine monitors have run into two main problems in detecting I-129. First because I-129 has a low specific activity (i.e., in comparison to other iodine fission products of spent fuel), has low-energy decay products, and because it is a minor iodine isotopic constituent in spent fuel, its detection by radio-counting techniques is often slow and impractical. The only means currently in use for measuring airborne radioactive constituents is radio-counting of the fission products. The counting techniques suffer from several shortcomings:

1. They are slow, requiring the collection of samples and offsight counting for extended periods of time. Thus real-time detection is not feasible;

2. Detecting concentrations of long-lived isotopes such as I-129 in the presence of backgrounds of such short-lived isotopes as $^{131}I_2$ is not practical;

3. The currently used counters are subject to failure under very high radioactivity levels such as might occur in a serious accident.

The second problem in detecting I-129 occurs because activated charcoal is the most widely used material employed for iodine removal and is also used as a means for decay storage. Because organic compounds of iodine are adsorbed less well than $I_2$ on activated charcoal substrates, in some applications charcoals are used which have been impregnated with substances which react chemically with $I_2$ and compounds of iodine or which undergo an isotopic exchange. Among examples currently used are charcoals impregnated with KI (or other inorganic iodine compounds) in which the stable isotope of the impregnant iodine can undergo an exchange (or reaction) with the radioiodine. Note that such an exchange can release a stable iodine into the effluent. For this reason detection instruments which rely on the ability to measure only the total iodine content in an effluent stream are unsatisfactory. The desired monitoring instrument must have the capability to detect only those iodine isotopes which are harmful and must be contained.

Although the present invention is an instrument designed to measure quantitatively, in real time, radioiodine concentration behind critical filter facilities, it may also be used;

(a) as a testing and trouble-shooting field measuring tool to test the integrity of in place filters;

(b) as a monitor of fairly high I-129 ambient concentrations in spent fuel reprocessing and;

(c) as a monitor to observe accidental large releases of radioiodine in the spent-fuel reprocessing cycle.

SUMMARY OF THE INVENTION

The present invention is a monitoring instrument to measure the concentration of I-129 in a gas, preferably air. The preferred apparatus utilizes a $^3He^{22}Ne$ laser. The laser beam is modulated and is incident on a sample gas chamber and a reference gas chamber. The sample gas chamber receives a continuous flow of air containing the concentration of I-129 to be measured. The reference gas chamber contains a reference sample of I-129 at a known concentration which will act as a reference from which the concentration of the I-129 sample in air will be measured.

The laser beam excites the I-129 molecules in both the sample and reference gas chambers to a metastable state which results in fluorescence emission from the I-129 molecule. The fluorescence from the sample and reference gas chamber are received by a pair of photomultipliers which convert the fluorescence emission to electrical signals. The electrical signals are fed to a detector which initially demodulates the signals. The signals are then each multiplied by a correction factor and divided to form a ratio. Since the concentration of the reference I-129 is known, the concentration of the I-129 sample in air may be computed from the ratio.

The novel feature of the invention lies in the specific lasing medium employed (i.e., $^3He^{22}Ne$) and the combination of using the laser, modulator, sample gas chamber, reference gas chamber, photomultipliers, and detector. This combination allows I-129 in air to be sampled continuously and have its concentration measured with high sensitivity with a mobile and cheap monitoring device.

In an alternative embodiment, the concentration of the sum of radioiodine isotopes may be measured by changing the wavelength of the laser.

In a second alternative embodiment the concentration of the I-129 in the sample gas may be measured directly from the photomultiplier output. Knowing this output, the concentration can be determined from the curves shown in FIG. 4.

In a third alternative embodiment a scrubber is added to the preferred embodiment to purify the I-129 sample to increase the sensitivity of the preferred embodiment.

DESCRIPTION OF THE PREFERRED EMBODIMENT

Figure 1:
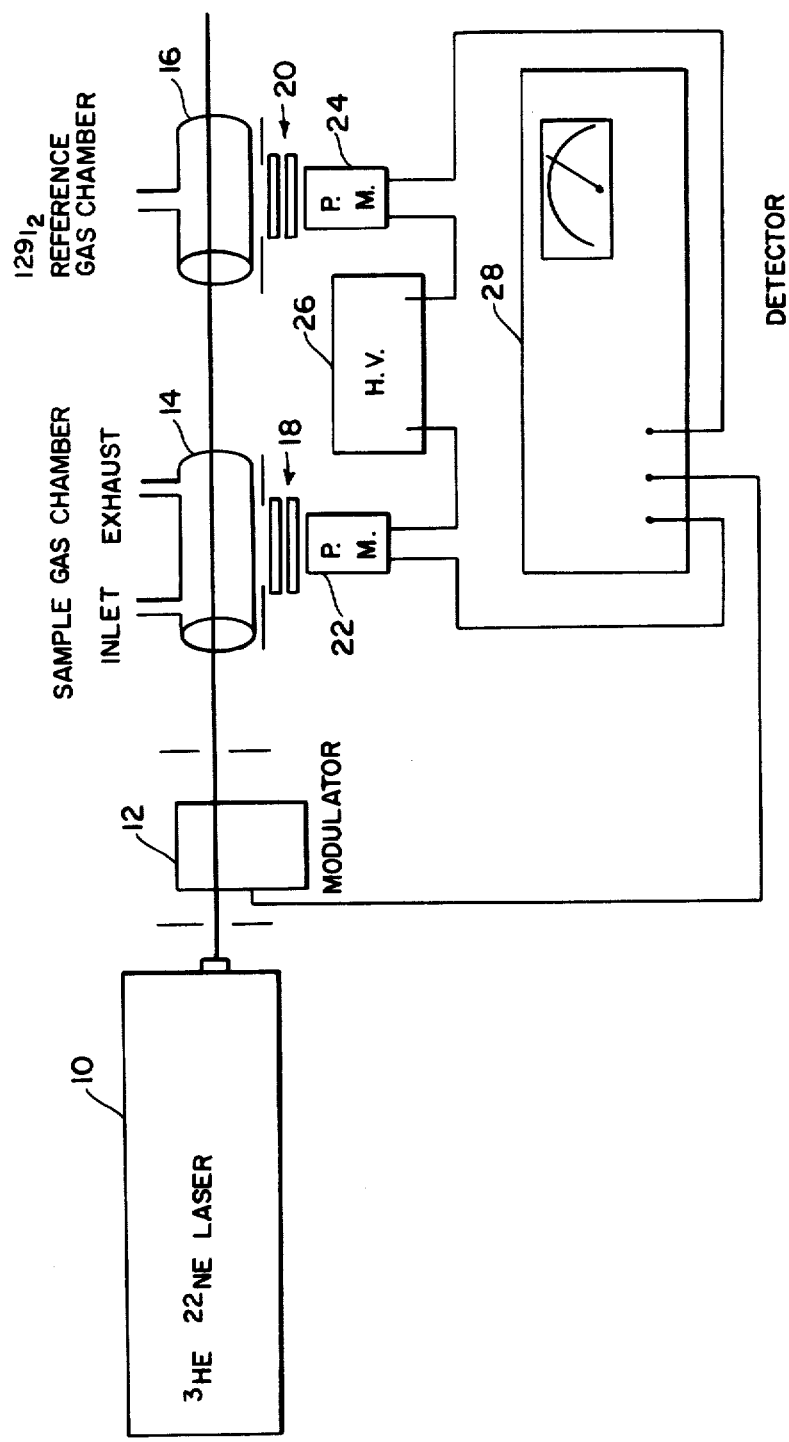
FIG. 1 is a block diagram of the apparatus for measuring the concentration of I-129 in a gas.

The apparatus for carrying out a laser-induced fluorescence measurement of I-129 concentrations is shown in FIG. 1. A laser 10 is a $^3He^{22}Ne$ laser configured for TEMoo operation at 6328 Å. An example of a laser which can be used is a Jodon Model HN-7 laser. The HN-7 laser used herein was specifically built to include $^3He^{22}Ne$ as the lasing gas because it has been found that its lasing frequencies excite I-129 atoms to a metastable state, but not other iodine isotope atoms. Also, this laser is very stable in output wavelength and amplitude (variations in wavelength may excite other iodine isotopes and variations in amplitude may give spurious I-129 concentration readings). The laser delivers 16 milliwatts and has five oscillating modes with a spacing of 260 MHz between modes. The gain curve of the laser and the respective oscillating modes of the laser superimposed on the gain curve are shown schematically in FIG. 3.

A modulator 12 modulates the laser beam at a low frequency such as 123 Hz. The modulator may be an electronic modulator or a mechanical chopper.

The modulated beam is incident on a sample gas chamber 14 which is a quartz cell having an inlet for allowing a gas sample to enter and an exhaust to allow the gas to leave. The sample gas will normally be air at atmospheric pressure which contains the I-129 isotope. The gas is continuously sampled.

A reference gas chamber 16 similar to sample gas chamber 14 also receives the modulated laser beam. The reference gas chamber contains a sample of I-129 at a known concentration. The chamber may be evacuated or contain a gas such as air or argon at a known pressure.

A sample filter 18 is made up of a combination of glass, long-wavelength-pass, sharp filters and a dielectric blocking filter which collectively reject the 6328 Å laser light and allow all fluorescence signals to pass. The filter is located adjacent sample gas chamber 14 and is used to isolate the fluorescence signal from scattered laser light. A reference filter 20 identical to the sample filter is located adjacent reference gas chamber 16 to eliminate scattered laser light from fluorescence signals from reference gas chamber 16.

A photomultiplier 22 is located behind filter 18. Photomultiplier 22 receives the fluorescence signal from filter 18. An identical photomultiplier 24 converts the fluorescence signal passing through filter 20 to an electrical signal. The photomultiplier may be an RCA 31000 A 2" photocathode extended S-20 response photomultiplier, for example. High-voltage source 26 provides power for operating photomultipliers 22, 24.

The outputs of photomultipliers 22, 24 are connected to a detector 28 which additionally receives a sample of the modulating signal from modulator 12. The signals are demodulated and are ready for further processing. The purpose of detector 28 is to determine the concentration of the I-129 in sample gas chamber 14 from the electrical signals received from photomultipliers 22, 24. Detector 28 does this by multiplying the two photomultiplier signals by correction factors and determining the ratio of the corrected signals. The principle of operation is that a known concentration of I-129 will result in a particular electrical signal output of photomultiplier 24. This output is ratioed with the output of photomultiplier 22. The ratio of the two photomultiplier outputs (as corrected) will be the same ratio as the ratio of the concentration of I-129 in the sample gas chamber to the concentration of the I-129 in the reference gas chamber. This relationship is as follows:

$$((\text{correction fac. 1})(\text{photomul. 22 output})/(\text{correction fac. 2})(\text{photomul. 24 output}) = (\text{Sample I-129 concentration/Reference I-129 concentration})$$

Therefore the I-129 concentration from the sample gas chamber may be computed from the known concentration of the I-129 in the reference gas chamber.

Figure 4:
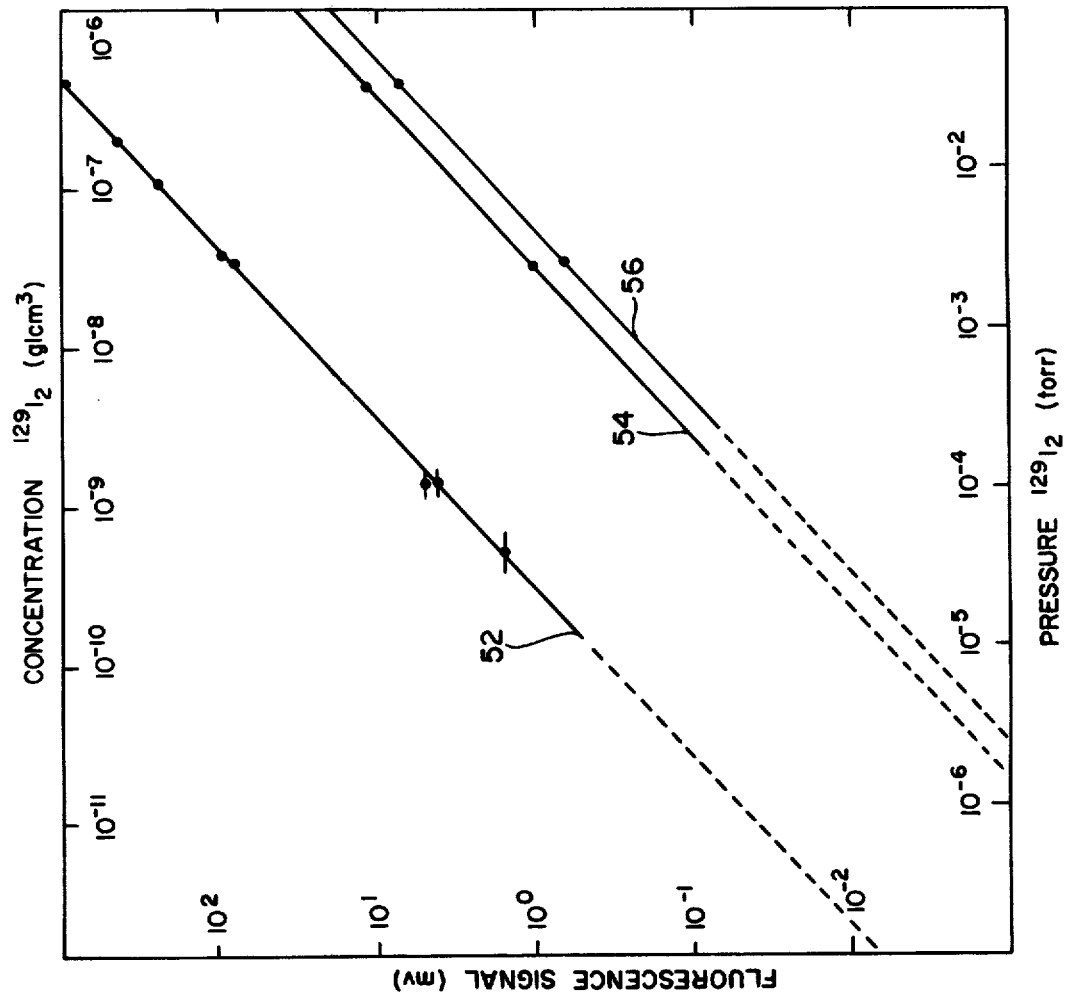
FIG. 4 is a graph of the measured fluorescence signal vs. I-129 concentration using the laboratory breadboard apparatus of FIG. 2.

The concentration of I-129 in sample gas chamber 14 could be determined solely from the output of photomultiplier 22 by observing the value of the photomultiplier output on curve 56 of FIG. 4 and reading the value of the I-129 concentration from the curve. This curve is the photomultiplier output plotted against I-129 concentration determined empirically using the test instrument shown in FIG. 2. However, the technique is insufficient because errors result from an unstable laser. By using a reference sample and a ratioing technique, the errors introduced by the laser are divided out in the computation of the ratio.

The correction factors for the photomultiplier output are needed because errors result from bimolecular quenching of $I_2$ fluorescence. In other words, when I-129 fluorescence is measured in a vacuum, a maximum value is obtained. This is shown in Curve 52 of FIG. 4. However, if I-129 is measured in the presence of another gas such as argon or air, the amount of fluorescence of I-129 produced is reduced by some factor. This is the correction factor referred to. For example, in the presence of Argon the fluorescence signals are decreased by a factor of 86 while in air the signals are decreased by a factor of 131.7 from the respective values under evacuated conditions. Curves 54 and 56 in FIG. 4 show the photomultiplier output values for argon and air. The bimolecular quenching process and the computation of the correction factor are well known and disclosed in J. I. Steinfeld, J. Chem. Phys, 44, 2740 (1966) and G. H. Capelle, H. P. Broida, J. Chem Phys, 58, 4212 (1973) hereby incorporated by reference. The bimolecular quenching process is dependent on pressure, the collision partner and the excitation wavelength. In the preferred embodiment of the invention the I-129 will be at atmospheric pressure in the presence of air in sample gas chamber 14; therefore the correction factor to be used in detector 28 will be 131.7.

In operation, the I-129 monitor shown in FIG. 1 may be placed behind a filter through which gas from a nuclear reactor passes to have radioactive materials removed (i.e., scrubbed). The monitor will detect I-129 if it passes through the filter.

A sample of the gas from the nuclear reactor coming through the filter is fed at atmospheric pressure into the inlet of sample gas chamber 14. Laser 10 produces a laser beam, having a wavelength of 6328 Å, which is incident on sample gas chamber 14. The energy from the laser beam is of the appropriate frequency to be absorbed by the I-129 molecule. The I-129 molecule absorbs the energy and is raised to a metastble excited electronic state. The excited I-129 molecule can relax by collisional processes back to the ground state in which case it will not be detected or it may relax by reemitting a photon (of longer wavelength) by a fluorescence mechanism. The emitted fluorescence passes out of sample gas chamber 14 and is filtered through filter 18 which blocks scattered laser light. The filtered fluorescence is detected by photomultiplier 22 and converted to an electrical signal which is fed to detector 28.

The laser beam is also incident on reference gas chamber 16 which contains a sample of I-129 in either a vacuum or in the presence of a gas such as air or argon. The concentration of I-129 is known. The laser beam raises the I-129 molecules to a metastable excited electronic state and a fluorescence emission is given off the same as in the sample gas chamber 14. The fluorescence emission is filtered by filter 20 and converted to an electrical signal by photomultiplier 24. The electrical signal is then fed to detector 28.

Since the I-129 in the reference gas chamber 16 may be in a vacuum or in a gas other than air at atmospheric pressure, the correction factor in detector 28 may be different than it is for the sample I-129 of sample gas chamber 14 (which is in air at atmospheric pressure). The detector will be built to have separate correction factors for the electrical signals for the sample and reference I-129.

Once the two electrical signals from photomultipliers 22, 24 are in detector 28 they will be demodulated by the signal from modulator 12. The reason for modulating the laser beam and demodulating the detected signal is to remove noise from the photomultiplier outputs. The photomultiplier output ideally is a D.C. signal but has frequency components from a few Hz to many MHz which are introduced by the photomultiplier. The modulation technique removes this noise. The technique is well known.

After the signals from photomultipliers 22, 24 (i.e., sample and reference signal respectively) are demodulated, both are multiplied by the appropriate correction factors and then divided to form a ratio. Once the ratio is known along with the known concentration of the reference I-129, then the concentration of I-129 in the sample gas chamber may be computed and read out on a meter.

If there is a requirement to measure much lower concentrations of I-129 than is feasible with the apparatus of FIG. 1, it is possible to extend the limits of sensitivity of the apparatus. This is done by using $I_2$ scrubbing techniques on larger samples of air to obtain a more purified sample containing $I_2$ and by measurement of I-129 in a carrier flow of helium in sample gas chamber 14. A correction factor for helium would have to be substituted for that of air during detection in detector 28.

The apparatus of FIG. 1 could also be easily adapted to measure the sum of radioiodine isotopes by changing the $^{22}$Ne gas in the laser to $^{20}$Ne and incorporating a tuning device or frequency-locking means. The resulting spectrum for the laser would cover excitation wavelengths for all radioiodine isotopes. The laser would then be tuned to an absorption line of a particular isotope and fluorescence from only this isotope would be detected. The laser is thus tuned through all possible isotopic combinations and the signals are summed.

Figure 2:
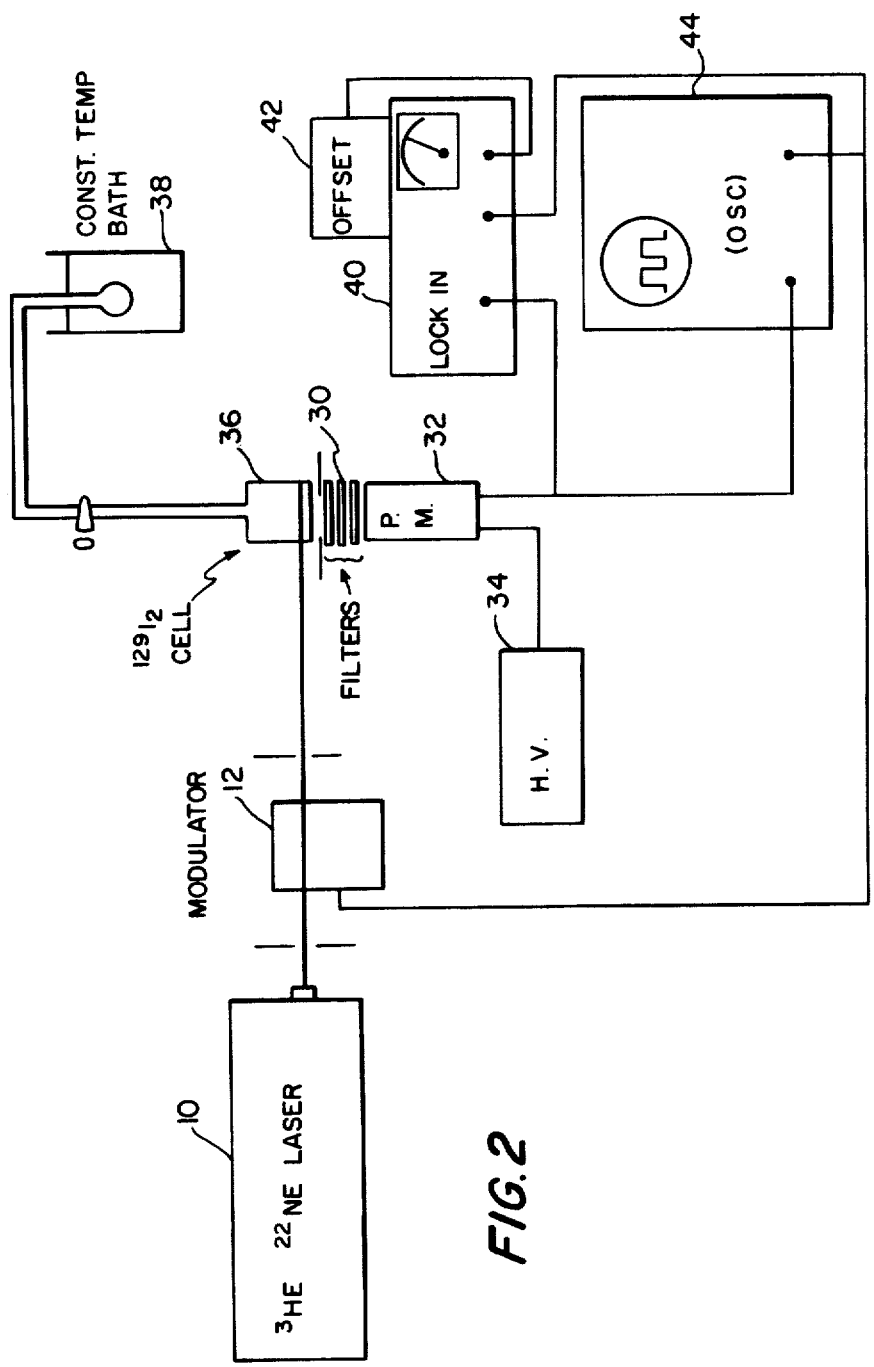
FIG. 2 is a block diagram of a laboratory breadboard model of the apparatus for measuring the signal from a sample of I-129 at a known concentration.

FIG. 2 shows a schematic of an operating laboratory model which was used to test the concept of using fluorescence emission to measure the concentration of I-129. Known concentrations of I-129 were subjected to laser excitation and readings of signal vs. concentration were measured. The readings are shown on FIG. 4. The $^3$He$^{22}$Ne laser 10, and modulator 12 are identical to those in FIG. 1. Filter 30, photomultiplier 32, and high voltage source 34 are the same respectively as filter 18, photomultiplier 22, and high voltage source 26 of FIG. 1. A cell 36 contains a sample of I-129 of a known concentration. The pressure in cell 36 is controlled by constant temperature bath 38 to keep the concentration constant.

The output of phtotmultiplier 32 is fed to a lock-in amplifier 40 (for example a P.A.R. model HR-8) which will demodulate the photomultiplier signal and provide an indication of the strength of the photomultiplier signal. Since the concentration of the tested sample is known beforehand and the lock-in amplifier is calibrated for these concentrations, the concentrations can be read out directly. An A.C. zero offset 42 (P.A.R. model 123) is used to null scattered laser light. An oscilloscope 44 measures various circuit parameters.

The experimental I-129 monitor was designed after solving the following problems:

(a) a laser excitation frequency had to be chosen which corresponded to an optical resonance of the specific molecule to be detected;

(b) excitation frequencies had to be selected which did not correspond to resonances of other species in the sample (i.e., other $I_2$ isotopes);

(c) evaluation had to be made of all non-fluorescing deactivation pathways which the selected molecule would undergo;

(d) possible fluorescing interferences from other species had to be accounted for;

(e) allowance had to be made for all possible molecular forms in which the atom to be detected could occur and appropriate corrections made.

Figure 3:
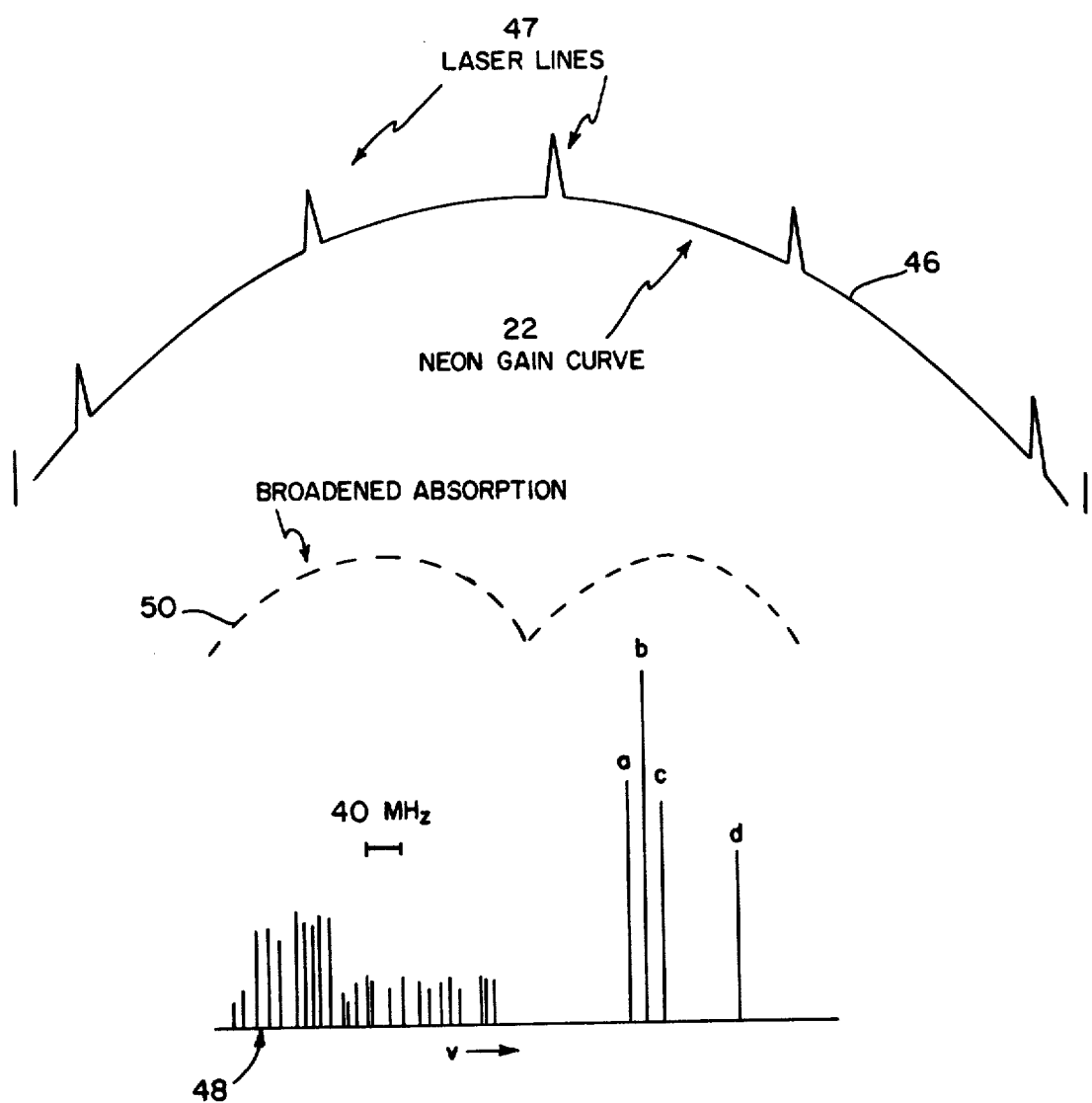
FIG. 3 shows the spectroscopic characteristics of the I-129 spectrum and the $^3He^{22}Ne$ laser.

FIG. 3 shows the spectral lines of laser 10 and the absorption band for I-129. Graphical line 36 shows the spectral lines for the operation of $^3$He$^{22}$Ne laser 10. The center wavelength of the laser is $\sim 6328$ Å. The five operating modes (i.e., frequencies at which the laser has an output) are about 260 MHz ápart.

Spectrum 48 shows the absorption band for I-129 under Doppler-free conditions. Spectrum 50 shows the spectrum of the absorption band for I-129 under atmospheric conditions. The spectral lines are smeared and a broadened spectrum results. The laser lines in the center of graphical line 46 provide the main excitation energy for the absorption band for I-129 of line 50.

FIG. 4 shows the results of testing various known concentrations of $I_2$ with the laboratory apparatus shown in FIG. 2. The fluorescence signal is shown in mv along the Y axis while the concentration of I-129 in (g/cm$^3$) is shown along the X axis. The concentration may also be expressed terms of pressure in torr.

Using the apparatus shown in FIG. 2, I-129 fluorescence signals were measured from two different fluorescence cells for two separate samples of I-129 over many repetitions at various temperatures in cells containing only I-129. Apparent pressure equilibrium was obtained in each case after ten minutes with a new temperature slush bath. Before and after each series of measurements the sample was frozen out at 77° K. to check the background correction factor. The upper curve in FIG. 4 shows a plot of fluorescence signal intensity as a function of I-129 pressure (and concentration). Measurements were made over iodine concentrations between B $5\times10^{-7}$ and $4\times10^{-10}$ g/cm$^3$. A good straight-line signal response was obtained over this range. For the lower concentration measurements, the ability to measure signals was not limited by the fluorescence signal, but by the uncertainty in the known vapor-pressure curves of $I_2$ as a function of temperature. The practical limits of sensitivity for fluorescence measurements are indicated by the dotted line extension of this curve. Since the signals follow a linear response curve, it is possible to measure in evacuated systems $I_2$ concentrations to near one picogram per $cm^3$. The working curve so obtained is in no way dependent upon a need to independently measure the absolute $I_2$ concentration by vapor-pressure curves or other techniques below the $10^{-10}$ $g/cm^3$ level.

The center and lower curves are fluorescence signal response for I-129 in static cell 36 in the presence of 1 atm of argon and 1 atm of air, respectively.

Obviously many modifications and variations of the present invention are possible in light of the above teachings. It is therefore to be understood that within the scope of the appended claims the invention may be practiced otherwise than as specifically described.

What is claimed and desired to be secured by Letters Patent of the United States is:

1. Apparatus for measuring the concentration of I-129 in a gaseous mixture including other iodine isotopes comprising:
    laser means for producing a laser beam of a wavelength of 6328 Å capable of raising said I-129 isotope to a metastable excited electronic state, said laser using $^3He^{22}Ne$ gas as the lasing medium;
    means for modulating said laser beam with a low frequency;
    sample gas-chamber means for receiving and containing a sample of said gas containing an I-129 isotope, said sample gas-chamber means having said laser beam incident thereon for generating fluorescence emissions from said I-129 isotope;
    reference gas-chamber means containing a reference sample of said I-129 isotope having a known concentration, said reference gas-chamber means having said laser beam incident thereon for generating fluorescence emissions from said I-129 reference;
    means for receiving and converting said fluorescence emission from said sample gas chamber to a sample electrical signal;
    means for receiving and converting said fluorescence emissions from said reference gas chamber to a reference electrical signal; and
    detector means receiving said sample and reference electrical signals for measuring the concentration of said I-129 isotopes therefrom.

2. The apparatus of claim 1 including filter means for receiving said fluorescence emissions from said sample gas chamber and said reference gas chamber for removing stray laser signals and passing said filtered fluorescence emissions to said means for receiving and converting fluorescence emission from said sample gas chamber and reference gas chamber respectively.

3. The apparatus of claim 2 in which said detector is a ratioing detector which will apply a correction factor to said sample and reference signals and then divide said signals to form a ratio, the concentration of said sample I-129 being determined from said ratio.

4. The apparatus of claim 2 in which said means for receiving and converting said fluorescence emissions from said sample gas chamber and said reference gas chamber are photomultipliers.

5. The apparatus of claim 2 in which said means for modulating in an electronic modulator.

6. The apparatus of claim 2 in which said means for modulating is a mechanical chopper.

7. The apparatus of claim 2 included:
    means for receiving and scrubbing said gas containing said I-129 isotope and for mixing said scrubbed gas with helium, said means for scrubbing providing an output to said sample gas chamber.

8. The apparatus of claim 2 in which:
    said detector is a ratioing detector which will apply a correction factor to said sample and reference signals and then divide said signals to form a ratio, said concentration of said I-129 being determined from said ratio;
    said means for receiving and converting said fluorescence emissions from said sample gas chamber and said reference gas chamber are photomultipliers; and
    said means for modulating is an electronic modulator.

9. A method for measuring the concentration of I-129 in a gas sample comprising the steps of:
    modulating the beam from a $^3He^{22}Ne$ laser with a low frequency signal;
    exciting a sample of said I-129 in a gas with said $^3He^{22}Ne$ laser beam to cause fluorescence emission,
    exciting a reference sample of a known concentration of I-129 with said $^3He^{22}Ne$ laser to cause fluorescence emission,
    filtering said fluorescence emission from said sample I-129,
    filtering said fluorescence emission from said reference I-129,
    converting said fluorescence emission from said sample I-129 to an electrical signal,
    converting said fluorescence emission from said reference I-129 to an electrical signal; and
    detecting said sample and reference I-129 electrical signals by demodulating said electrical signals, applying a correction factor to said electrical signals, and dividing said electrical signals to form a ratio from which the concentration of I-129 in said sample gas is determined.

* * * * *